United States Patent
Kim

(10) Patent No.: US 11,125,841 B2
(45) Date of Patent: Sep. 21, 2021

(54) RADIO FREQUENCY COIL AND MAGNETIC RESONANCE IMAGING SYSTEM COMPRISING THE SAME

(71) Applicant: Samsung Electronics Co., Ltd., Suwon-si (KR)

(72) Inventor: Kyoungnam Kim, Incheon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 563 days.

(21) Appl. No.: 15/503,442

(22) PCT Filed: Jan. 21, 2015

(86) PCT No.: PCT/KR2015/000620
§ 371 (c)(1),
(2) Date: Feb. 13, 2017

(87) PCT Pub. No.: WO2016/024677
PCT Pub. Date: Feb. 18, 2016

(65) Prior Publication Data
US 2017/0234947 A1    Aug. 17, 2017

(30) Foreign Application Priority Data
Aug. 11, 2014  (KR) .................. 10-2014-0103627

(51) Int. Cl.
*G01R 33/34* (2006.01)
*A61B 5/055* (2006.01)

(52) U.S. Cl.
CPC ........ *G01R 33/34076* (2013.01); *A61B 5/055* (2013.01); *G01R 33/34007* (2013.01)

(58) Field of Classification Search
CPC ........ G01R 33/34007; G01R 33/34076; G01R 33/34046; A61B 5/055
See application file for complete search history.

(56) References Cited

U.S. PATENT DOCUMENTS 4,920,318 A * 4/1990 Misic ............... G01R 33/34046
324/318
5,309,104 A    5/1994 Frederick
(Continued)

FOREIGN PATENT DOCUMENTS

JP          7-370 A      1/1995
JP       7-323017 A    12/1995
(Continued)

OTHER PUBLICATIONS

English translation of JP 2000-189397. Provided by Espacenet. (Year: 2020).*
(Continued)

*Primary Examiner* — Rishi R Patel
(74) *Attorney, Agent, or Firm* — NSIP Law

(57) ABSTRACT

A radio frequency (RF) coil and a magnetic resonance imaging (MRI) system including the same are provided. The RF coil may include at least one RF coil element formed on a base of a cylindrical shape having a circular or oval cross-sectional shape, wherein coil elements of a first end portion and a second end portion of the at least one RF coil element have regions surrounding an outer circumferential portion of the base and bent in a z axis direction. The at least one RF coil element may include a first RF coil element and a second RF coil element.

19 Claims, 8 Drawing Sheets

(56) References Cited

U.S. PATENT DOCUMENTS

| | | | | |
|---|---|---|---|---|
| 5,372,137 | A | * | 12/1994 | Wong .................. A61B 5/0555 |
| | | | | 324/309 |
| 6,011,395 | A | * | 1/2000 | Leifer .............. G01R 33/34046 |
| | | | | 324/318 |
| 8,022,705 | B2 | * | 9/2011 | Bogdanov ........ G01R 33/34046 |
| | | | | 324/318 |
| 2005/0146331 | A1 | * | 7/2005 | Flexman .................. H01Q 7/00 |
| | | | | 324/318 |
| 2006/0173284 | A1 | * | 8/2006 | Ackerman ....... G01R 33/34046 |
| | | | | 600/422 |
| 2006/0267588 | A1 | | 11/2006 | Okamoto et al. |
| 2007/0079253 | A1 | * | 4/2007 | Leussler .......... G01R 33/34046 |
| | | | | 715/784 |
| 2010/0102817 | A1 | | 4/2010 | Saha |
| 2010/0175100 | A1 | | 7/2010 | Ogasawara |
| 2011/0204890 | A1 | * | 8/2011 | Habara ............ G01R 33/34046 |
| | | | | 324/307 |

FOREIGN PATENT DOCUMENTS

| | | | |
|---|---|---|---|
| JP | 2000-189397 | A | 7/2000 |
| JP | 3442478 | B2 | 9/2003 |
| JP | 2005-245798 | A | 9/2005 |
| JP | 2014-10090 | A | 1/2014 |
| JP | 2014-42685 | A | 3/2014 |

OTHER PUBLICATIONS

Patrice Boissoles, et al., "Magnetic field properties in a birdcage coil," *HAL archives-ouvertes.fr*, vol. 6-13, Mar. 15, 2006, pp. 1-11 (13 pages, in English).

Sonal Josan, et al., "Application of Double Spin-Echo Spiral Chemical Shift Imaging to Rapid Metabolic Mapping of Hyperpolarized [1-$^{13}$C]-Pyruvate," *J Magn Reson, NIH Public Access*, Apr. 2011, vol. 209(2), pp. 1-12.

International Search Report dated May 11, 2015, in counterpart International Application No. PCT/KR2015/000620 (2 pages in English, 3 pages in Korean).

Korean Office Action dated Oct. 29, 2020 in counterpart Korean Patent Application No. 10-2014-0103627 (5 pages in English and 5 pages in Korean).

* cited by examiner

RADIO FREQUENCY COIL AND MAGNETIC RESONANCE IMAGING SYSTEM COMPRISING THE SAME

CROSS-REFERENCE TO RELATED APPLICATIONS

This application is a U.S. National Stage application of International Application No. PCT/KR2015/000620 filed on Jan. 21, 2015 and published as WO 2016/024677 A1 on Feb. 18, 2016, which claims the benefit under 35 USC 119(a) of Korean Patent Application No. 10-2014-0103627 filed Aug. 11, 2014, in the Korean Intellectual Property Office, the entire disclosures of which are incorporated herein by reference for all purposes.

TECHNICAL FIELD

The present disclosure relates to a radio frequency (RF) coil and a magnetic resonance imaging (MRI) system including the same.

BACKGROUND ART

Diverse diagnostic apparatuses for diagnosing an abnormality in a physical body have been used to prevent and cure diseases. Among them, a magnetic resonance imaging (MRI) apparatus that uses a magnetic field generated by a magnetic force is widely used.

The MRI apparatus is used to obtain a sectional image of a subject (e.g., a human body) by using the NMR phenomenon. Owing to the NMR phenomenon, some atomic nuclei (e.g., hydrogen ($^1$H), phosphorus ($^{31}$P), sodium ($^{23}$Na), carbon isotope ($^{13}$C), and so forth) existing in a human body have their own rotating magnetic field constants. Accordingly, if an electromagnetic wave is applied to a magnetization vector of such an atomic nucleus, the magnetization vector may lie on a vertical plane owing to the resonance of the magnetization vector, and a magnetic resonance signal to be produced from the magnetization vector may be used to obtain an internal image of the human body. Here, an RF coil may be used to transmit an electromagnetic wave for inducing the resonance of the magnetization vector in the human body and to receive the magnetic resonance signal produced from the magnetization vector lying on the vertical plane owing to the resonance. Given that the RF coil is used to transmit an electromagnetic wave for the resonance of the magnetization vector and to receive the magnetic resonance signal, the RF coil may also be called an RF antenna. A single RF coil or antenna may be used not only to induce the resonance of the magnetization vector (in a transmission mode) but also to receive the magnetic resonance signal (in a reception mode), and in certain cases, two different RF coils may be used to separately perform the transmission mode and the reception mode. A single coil configured to perform in both the transmission and reception modes is called a transceiving coil, a coil for the transmission mode is called a transmission coil, and a coil for the reception mode is called a reception coil.

Meanwhile, the RF coil may include a body-type RF coil, which is provided in an exterior part of an MRI device, and a surface-type RF coil or a volume-type RF coil, which is attached to, or positioned adjacent to, a human body. Since the body-type RF coil is provided in the exterior part of the MRI device, it may be formed on a cylinder-shaped frame that has a size allowing an object to be entered therein and it may be used as the transceiving or transmission coil.

Meanwhile, the surface- or volume-type RF coil may be attached to an object and may be attachably/detachably provided to a table on which a human body lies. Generally, the surface or volume-type RF coil may be produced to have a shape suitable for a part of a human body, and thus, it may include a head coil, a neck coil, a waist coil, and so forth. Furthermore, the surface or volume-type RF coil may be used as the transceiving or reception coil.

DETAILED DESCRIPTION OF THE INVENTION

Technical Problem

Provided are a radio frequency (RF) coil, in particular, a volume-type RF coil, capable of forming a magnetic field corresponding to a region of interest (ROI) of an object in a magnetic resonance imaging (MRI) system and the MRI system including the same. The technical problem to be solved by the present embodiment is not limited to the above-described technical problem and may further include other technical problems.

Technical Solution

In an embodiment of the present invention, a radio frequency (RF) coil for a magnetic resonance imaging (MRI) system is provided. The RF coil includes: at least one RF coil element formed on a base of a cylindrical shape having a circular or oval cross-sectional shape, wherein coil elements of a first end portion and a second end portion of the at least one RF coil element have regions surrounding an outer circumferential portion of the base and bent in a z axis direction.

The RF coil may form a magnetic field of an asymmetrical shape in a z direction with respect to a y axis on a z-y plane.

The at least one RF coil element may include connectors formed by connecting the coil element of the first end portion and the coil element of the second end portion.

The connectors may be formed in a straight line shape in a z axis direction between the coil element of the first end portion and the coil element of the second end portion.

8 through 32 connectors may be formed.

The at least one RF coil element may have a shape that is bent in a z axis direction and protrudes such that end-ring parts of end portions of birdcage-type coils alternate each other.

The at least one RF coil element may include a first RF coil element and a second RF coil element, wherein directions in which the first RF coil element and the second RF coil element protrude in the z axis direction alternate each other.

Shapes of magnetic fields formed by the first RF coil element and the second RF coil element may alternate each other in a diagonal direction on a z-y plane.

An insulating layer may be formed between the first RF coil element and the second RF coil element in order to maintain an electrical insulation.

The RF coil may be a volume-type RF coil

Also, in the present disclosure, an MRI system is provided. An RF coil includes at least one RF coil element formed on a base of a cylindrical shape having a circular or oval cross-sectional shape, wherein coil elements of a first end portion and a second end portion of the at least one RF coil element have regions surrounding an outer circumferential portion of the base and bent in a z axis direction.

The RF coil may be a volume-type RF coil located on a table on which an object is located.

Advantageous Effects of the Invention

According to an embodiment of the present disclosure, in an MRI system, volume-type RF coils are asymmetrically arranged in a z axis direction, and thus magnetic fields may be distributed in a diagonal direction on an x-z plane or on a y-z plane.

According to an embodiment of the present disclosure, a volume RF coil capable of adjusting a distribution of magnetic fields according to a region of interest (ROI) of an object and an MRI system including the same may be provided.

DETAILED DESCRIPTION

Figure 1:
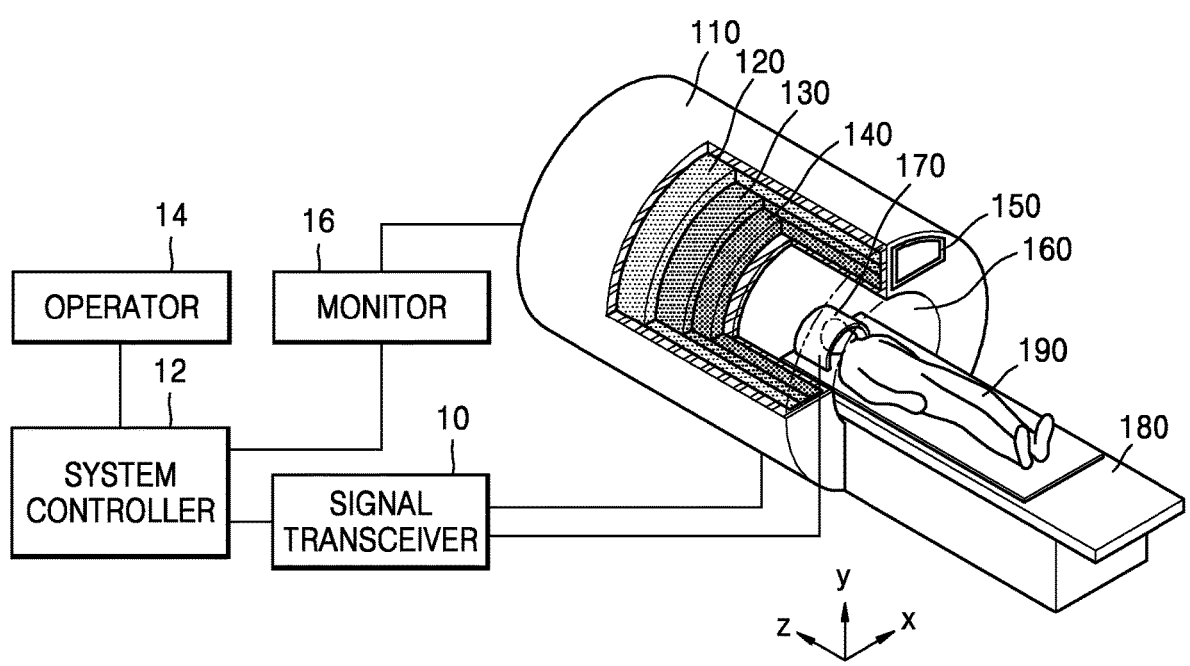
FIG. 1 is a schematic diagram of a structure of a magnetic resonance imaging (MRI) system according to an embodiment of the present invention.

A radio frequency (RF) coil and a magnetic resonance imaging (MRI) system including the same according to an embodiment of the present invention will now be described in detail with reference to the accompanying drawings below. Sizes or thicknesses of layers or regions shown in the accompanied drawings are somewhat exaggerated for clarity of the specification. Throughout the detailed description, like reference numerals denote like elements.

FIG. 1 is a schematic diagram of a structure of an MRI system according to an embodiment of the present invention.

Referring to FIG. 1, the MRI system may include a main magnet 120 inside a housing 110, a gradient coil 130, and a body-type RF coil 140.

The main magnet 120 may generate a magnetostatic field or a static magnetic field for aligning, in a constant direction, a direction of magnetic dipole moments of atomic nuclei of elements causing magnetic resonance, such as hydrogen, phosphorous, or sodium, from among elements distributed in an object 190. The main magnet 120 may use, for example, a superconducting magnet that generates a high magnetic field that is equal to or higher than 0.5 T. As the magnetic field generated by the main magnet 120 is strong and uniform, a more precise and accurate magnetic resonance image with respect to the object 190 may be obtained.

For reference, in the present specification, an "object" 190 may include a person or an animal or a part of a person or an animal. For example, the object 190 may include the liver, the heart, the womb, the brain, the breast, the abdomen, or a blood vessel.

The gradient coil 130 may be formed at an inner side of the main magnet 120. The gradient coil 130 may include three gradient coils for generating gradient magnetic fields in X-, Y-, and Z-axis directions crossing each other at right angles. The gradient coil 130 may generate a spatially linear gradient magnetic field for photographing a magnetic resonance image. The gradient coil 130 may provide location information of each region of the object 190 by differently inducing resonance frequencies according to the regions of the object 190.

The body-type RF coil 140 may be mounted at an inner side of the gradient coil 130. The body-type RF coil 140 may be included in the cylindrical-shaped magnetic structure, together with the main magnet 120 and the gradient coil 130. Also, a volume-type RF coil 170 or a surface-type RF coil may be located adjacent to the object 190 on a table 180 on which the object 190 is located.

The RF coils 140 and 170, i.e. the body-type RF coil 140, the volume-type RF coil 170, and the surface-type RF coil, may be devices capable of generating a high frequency magnetic field having a Lamor frequency as a main frequency, may irradiate an RF signal onto the object 190, and receive a magnetic resonance signal emitted from the object 190. In more detail, in order to make an atomic nucleus transit from a low energy state to a high energy state, the body-type RF coil 140, the volume-type RF coil 170, and the surface-type RF coil may generate and apply an electromagnetic wave signal having an RF corresponding to a-type of the atomic nucleus, for example, an RF signal, to the object 190. When the electromagnetic wave signal generated by the body-type RF coil 140 and the volume-type RF coil 170 is applied to the atomic nucleus, the atomic nucleus may transit from the low energy state to the high energy state. Then, when electromagnetic waves generated by the body-type RF coil 140 and the volume-type RF coil 170 disappear, the atomic nucleus, on which the electromagnetic waves were applied transits from the high energy state to the low energy state, thereby emitting electromagnetic waves having a Lamor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Lamor frequency. The body-type RF coil 140 and the volume-type RF coil 170 may receive electromagnetic wave signals from atomic nuclei of the object 190. If the received electromagnetic wave signals are amplified by a high frequency amplifier and then are demodulated with Larmor frequency sine waves, baseband magnetic resonance signals may be obtained. The baseband magnetic resonance signals may be image processed, and thus a magnetic resonance image may be generated.

The body-type RF coil 140 may be fixed at the inner side of the gradient coil 130 of the housing 110. The volume-type RF coil 170 may be detachable from the table 180 on which the object 190 is located. The volume-type RF coil 170 may be used to diagnose a specific region of the object 190, for example, the head, the face, the legs, or the ankles, etc. of the object 190, or a relatively small-sized object.

The housing 110 including the main magnet 120, the gradient coil 130, and the body-type RF coil 140 may have a cylindrical shape. A bore 160, which is a space into which the table 100 on which the object 190 is located may enter, may be formed in the housing 110. The bore 160 may extend into the body-type RF coil 140 in the z-axis direction. A diameter of the bore 160 may be determined according to sizes of the main magnet 120, the gradient coil 130, and the body-type RF coil 140.

A display 150 may be mounted at an outer side of the housing 110 of the MRI system. A display may further be included at an inner side of the housing 110. Certain information may be transmitted to a user or the object 190 through the display(s) located at the inner side and/or the outer side of the housing 110. Also, the MRI system may include a signal transceiver 10, a system controller 12, a monitor 14, and an operator 16. The signal transceiver 10 may control a gradient magnetic field formed in the housing 110, that is, the bore 160, and may control transmission and reception of an RF signal and a magnetic resonance signal related to the body-type RF coil 140 and the volume-type RF coil 170. The system controller 12 may control sequence of signals generated in the housing 110. The monitor 14 may monitor or control the housing 110 or various devices mounted in the housing 110. The operator 16 may control overall operations of the MRI system.

Figure 2:
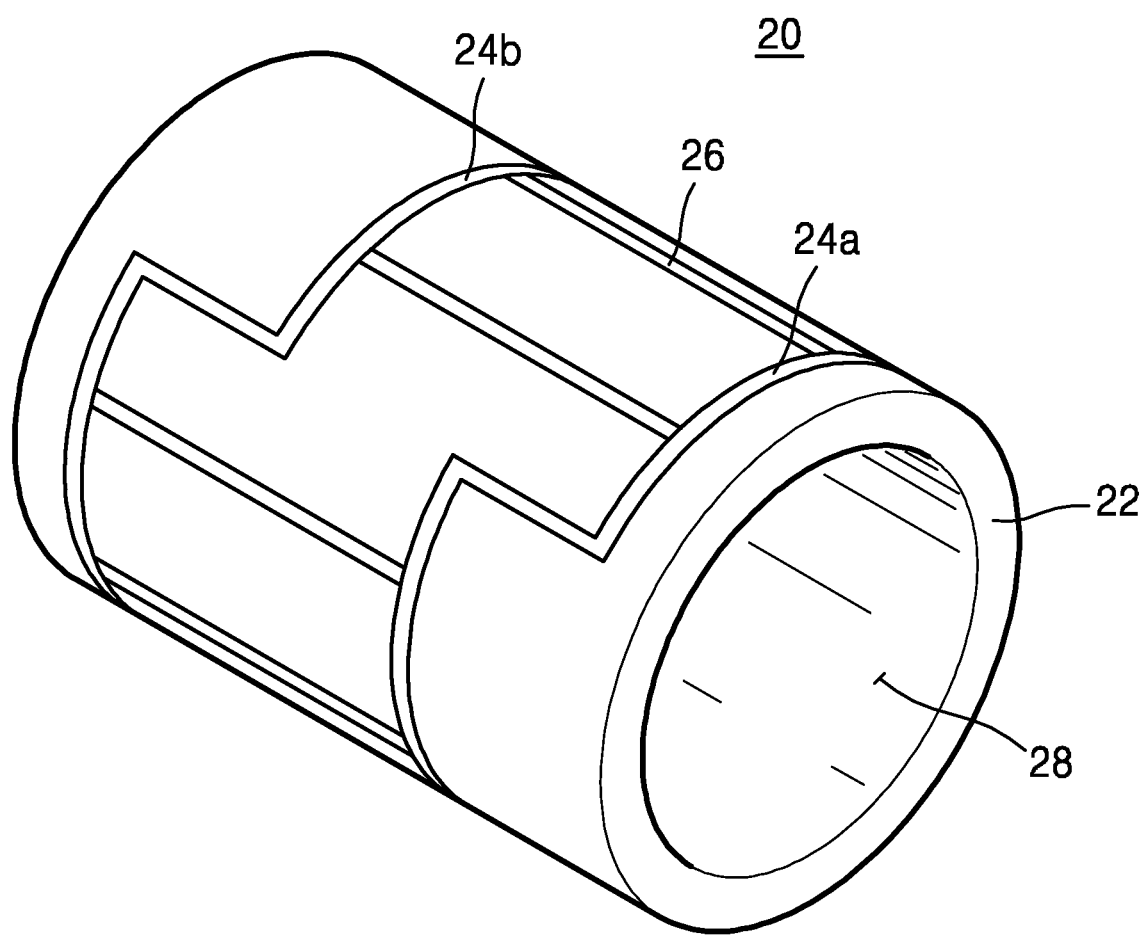
FIG. 2 illustrates an example of an RF coil of an MRI system according to an embodiment of the present invention.

FIG. 2 illustrates an example of an RF coil 20 of an MRI system according to an embodiment of the present invention. The RF coil 20 may be the volume-type RF coil 170 adjacent to the object 190 of FIG. 1 but the RF coil 20 may also applied to the body-type RF coil 140.

Referring to FIG. 2, the RF coil 20 may have a structure including RF coil elements 24a, 24b, and 26 formed on a base 22. The RF coil elements 24a, 24b, and 26 may have a shape that is bent in a z axis direction and protrudes such that end-ring parts of end portions of birdcage-type coils alternate each other. Specifically, the coil elements 24a and 24b of a first end portion and a second end portion of the RF coil elements 24a, 24b, and 26 may have a ring shape surrounding an outer circumferential portion of the base 22 and may have a region bent in the z axis direction. A plurality of connectors 26 may be formed between the coil element 24a of the first end portion and the coil element 24b of the second end portion of the RF coil elements 24a, 24b, and 26. The connectors 26 may be presented as legs, rods, etc. and may be formed in a straight line shape in the z direction. A cavity 28, which is an empty space into which a certain part of the object 190 of FIG. 1 may enter, may be formed in an inner side of the base 22 of the RF coil 20. The cavity 28 may be formed in the z axis direction. A specific part of the object 190, for example, the head, the face, the legs, or the ankles, etc. of the object 190, or a relatively small-sized object may enter into the cavity 28.

The first coil element 24a and the second coil element 24b of the second end portion of the RF coil elements 24a, 24b, and 26 may act as paths for moving an RF source such as current or voltage, etc. applied to the RF coil 20. A large number of connectors 26 of the RF coil elements 24a, 24b, and 26 may be used between the coil elements 24a and 24b of the first end portion and the second end portion in order to enhance homogeneity and sensitivity of a magnetic field that may be generated from the RF coil 20. However, the number of connectors 26 is not limited thereto. When an infinite number of connectors 26 are theoretically formed, although the homogeneity and sensitivity of the magnetic field are ideally enhanced, since there is mutual inductance coupling between the connectors 26, an infinite increase is limited. In the present disclosure, for example, 8 through 32 connectors 26 between the coil element 24a of the first end portion and the coil element 24b of the second end portion of the RF coil elements 24a, 24b, and 26 may be formed but are not limited thereto.

The base 22 of the RF coil 20 may include a rigid and relatively light material and may include a non-magnetic material which has excellent corrosion resistance and moldability. Specifically, the base 22 may include an insulating polymer and a plastic material, for example, fiber reinforced plastics (FPR) among glass fiber reinforced plastics (GFRP). An end portion of the base 22 may have a circular or oval cylindrical shape. The coil element 24a of the first end portion and the coil element 24b of the second end portion of the RF coil elements 24a, 24b, and 26, and the connectors 26 may include a conductive material and, for example, may be formed by patterning a metallic material having high electrical conductivity, such as copper, silver, or gold coated copper, but are not limited thereto. Capacitors may be formed in the coil element 24a of the first end portion and the coil element 24b of the second end portion of the RF coil elements 24a, 24b, and 26, and the connectors 26. The RF coil 20 according to the present disclosure may be applied as a transceiving RF coil.

Figure 3A:
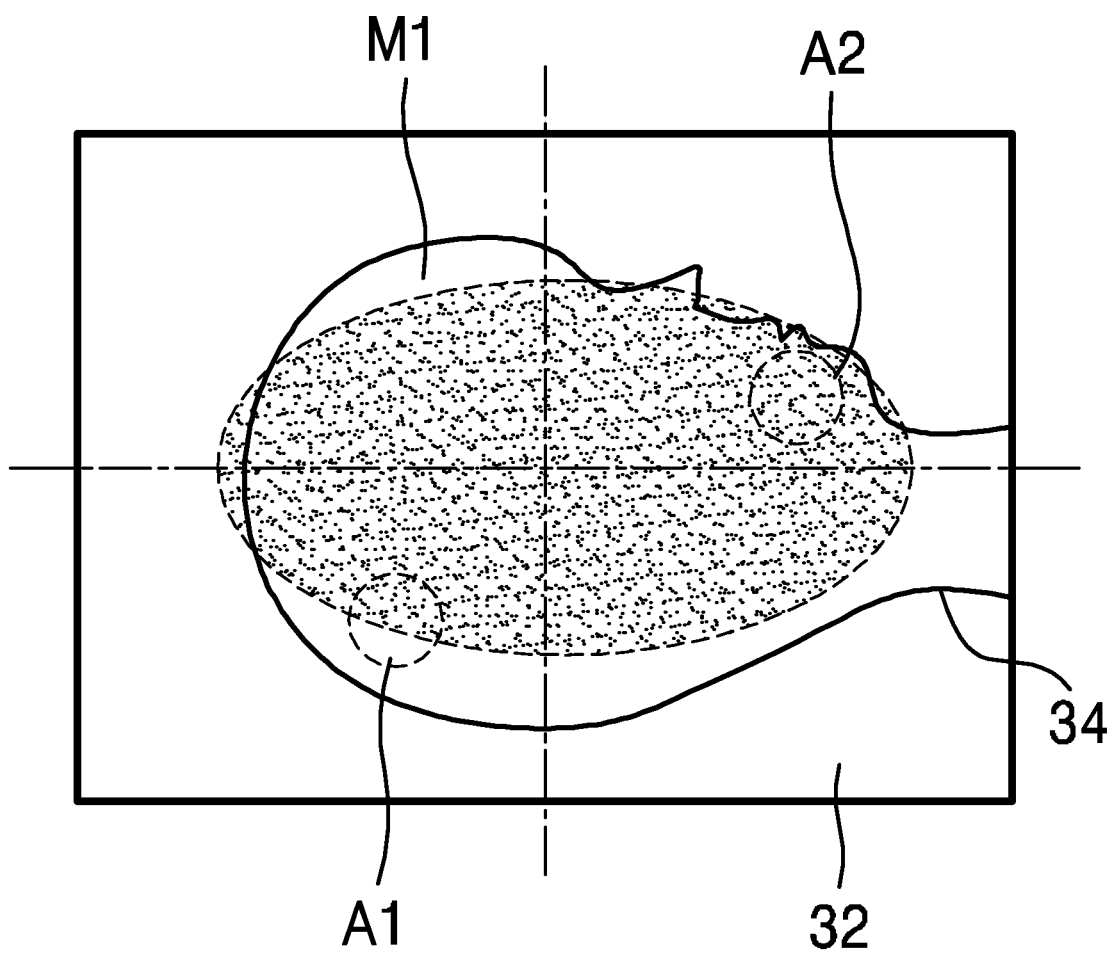
FIG. 3A illustrates a magnetic field formed when an object is located in an RF coil.

FIG. 3A illustrates a magnetic field M1 formed when an object 34 is located in an RF coil 32. The volume-type RF coil 32 of a general-type, for example, the RF coil 32 using a birdcage coil, is illustrated.

Referring to FIG. 3A, when the object 34 is located in the RF coil 32, in a general birdcage-type coil, the magnetic field M1 that is uniform on an x-y plane and has a symmetrical signal refocusing profile in a z axis direction with respect to a y axis may be formed. However, the signal refocusing may deteriorate from a center region to a peripheral region and in a diagonal direction. For example, when a region A1 and a region A2 of the object are regions of interest (ROIs), it may not be easily to obtain a uniform MRI.

Figure 3B:
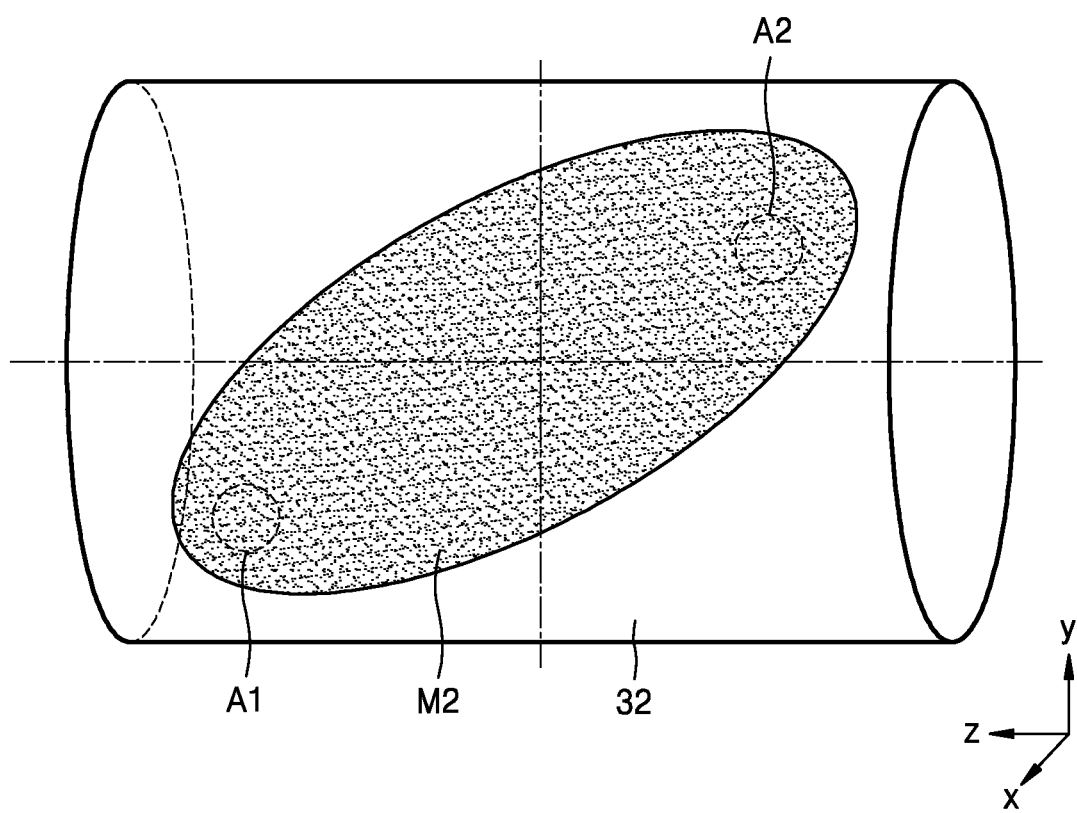
FIG. 3B illustrates a magnetic field formed by an RF coil according to an embodiment of the present invention.

FIG. 3B illustrates a magnetic field M2 formed by the RF coil 32 according to an embodiment of the present invention.

Referring to FIG. 3B, in the RF coil 32 including the RF coil elements 24a, 24b, and 26 of FIG. 2, the magnetic field M2 that has an asymmetrical shape in a z axis direction with respect to a y axis on a z-y plane may be formed. When the magnetic field M2 is formed and even when the region A1 and the region A2 of the object 34 are regions of interest (ROIs), since the magnetic field M2 is included in a uniform region, a uniform MRI may be obtained. As described above, according to the present disclosure, the RF coil having a shape corresponding to the ROIs of the object 34 may be provided, a central region of the RF coil portion may have a high B1 sensitivity, and a generally uniform magnetic field distribution may be obtained in a magnetic field M2-forming region, for example, in the magnetic field M2 formed in a diagonal direction on the z-y plane.

Figure 4A:
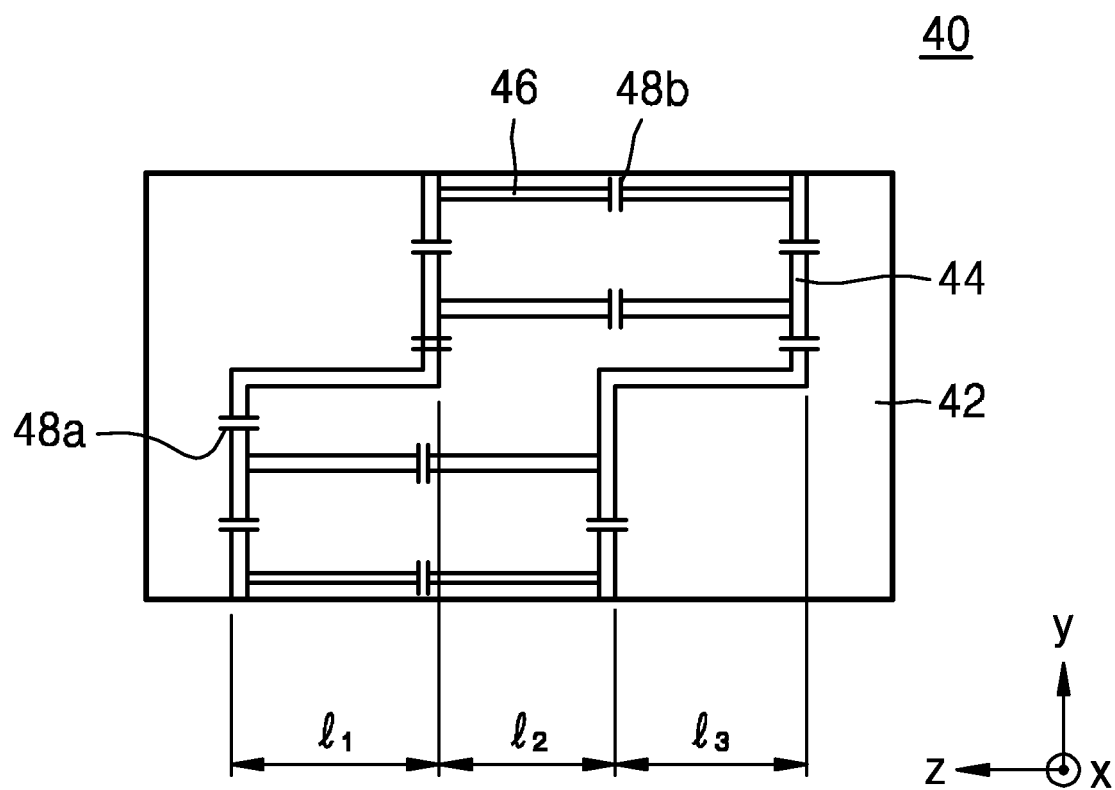
FIG. 4A is a lateral diagram of an RF coil according to an embodiment of the present invention.
Figure 4B:
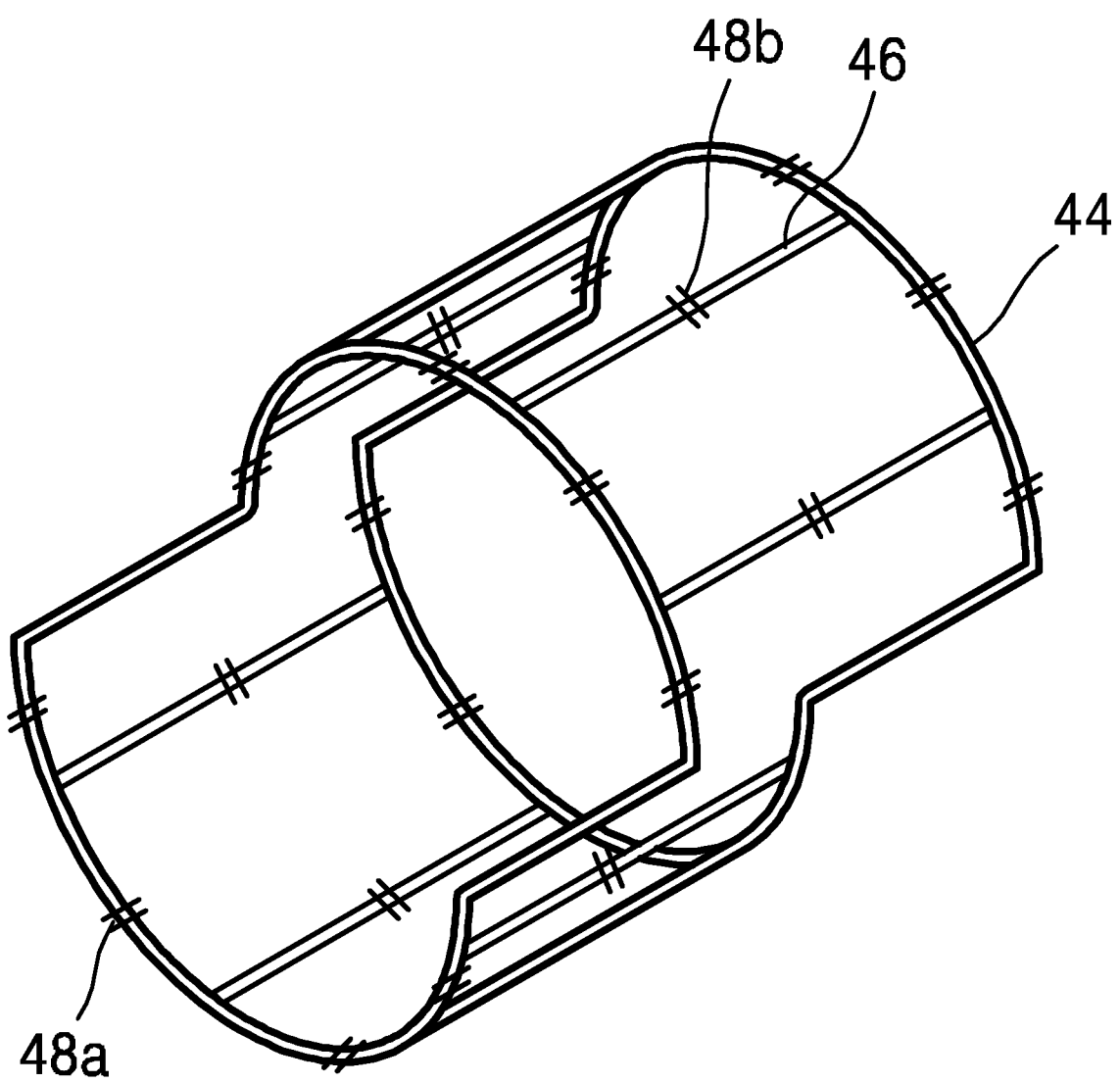
FIG. 4B illustrates RF coil elements of an RF coil according to an embodiment of the present invention.

FIG. 4A is a lateral diagram of an RF coil 40 according to an embodiment of the present invention. FIG. 4B illustrates RF coil elements 44 and 46 of the RF coil 40 according to an embodiment of the present invention.

Referring to FIGS. 4A and 4B, the RF coil 40 may have a structure including the RF coil elements 44 and 46 formed on a base 42. The coil elements 44 of an end portion of the RF coil elements 44 and 46 may include regions l1 and l3 that are respectively bent and protrude in +z and −z directions from a center region l2. In this regard, a ratio of the center region l2 and the regions l1 and l3 that are respectively bent and protrude in the +z and −z directions may be selectively determined according to a shape of a magnetic field to be formed. For example, the ratio of l1:l2:l3 of the center region l1 of the RF coil elements 44 and 46 and the regions l1 and l3 that are respectively bent and protrude in the +z and −z directions may be 1:1:1 and may be 0.5:1:0.5.

The coil elements 44 of the end portion of the RF coil elements 44 and 46 of the RF coil 40 according to the present disclosure may have a bent part at a part corresponding to about a middle of a height in a y direction with respect to a lateral or sagittal view but is not limited thereto. Capacitors 48a and 48b may be respectively formed in the coil elements 44 of the end portion of the RF coil elements 44 and 46 and connectors 46 between the coil elements 44 of the end portion.

Figure 5A:
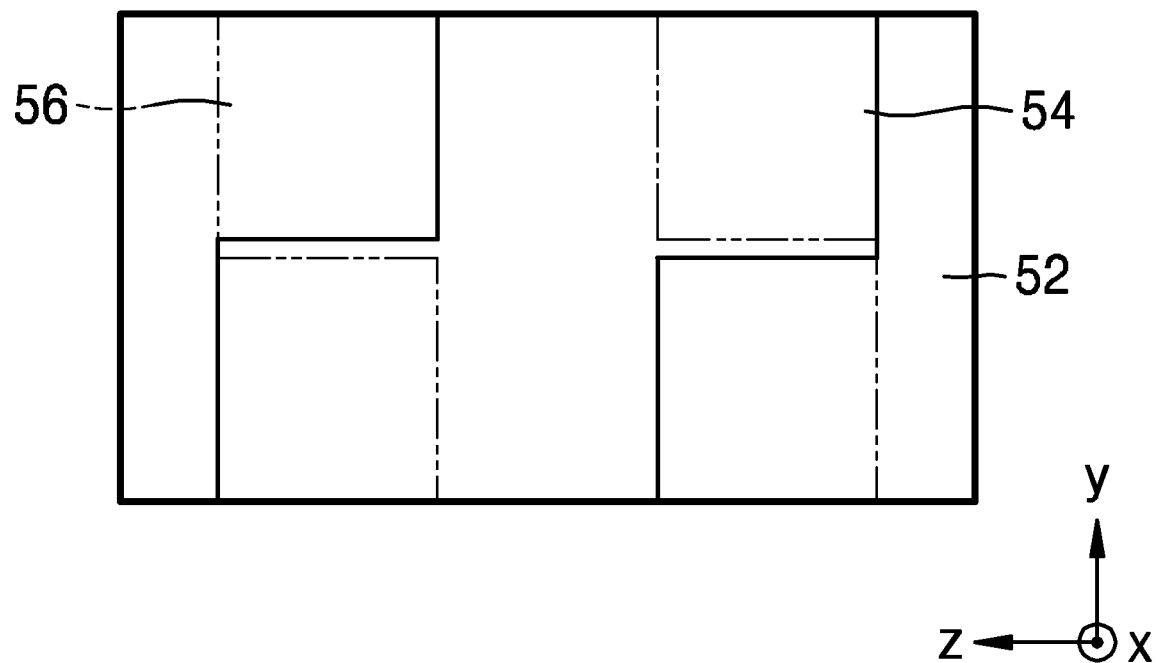
FIG. 5A illustrates an RF coil according to another embodiment of the present invention.
Figure 5B:
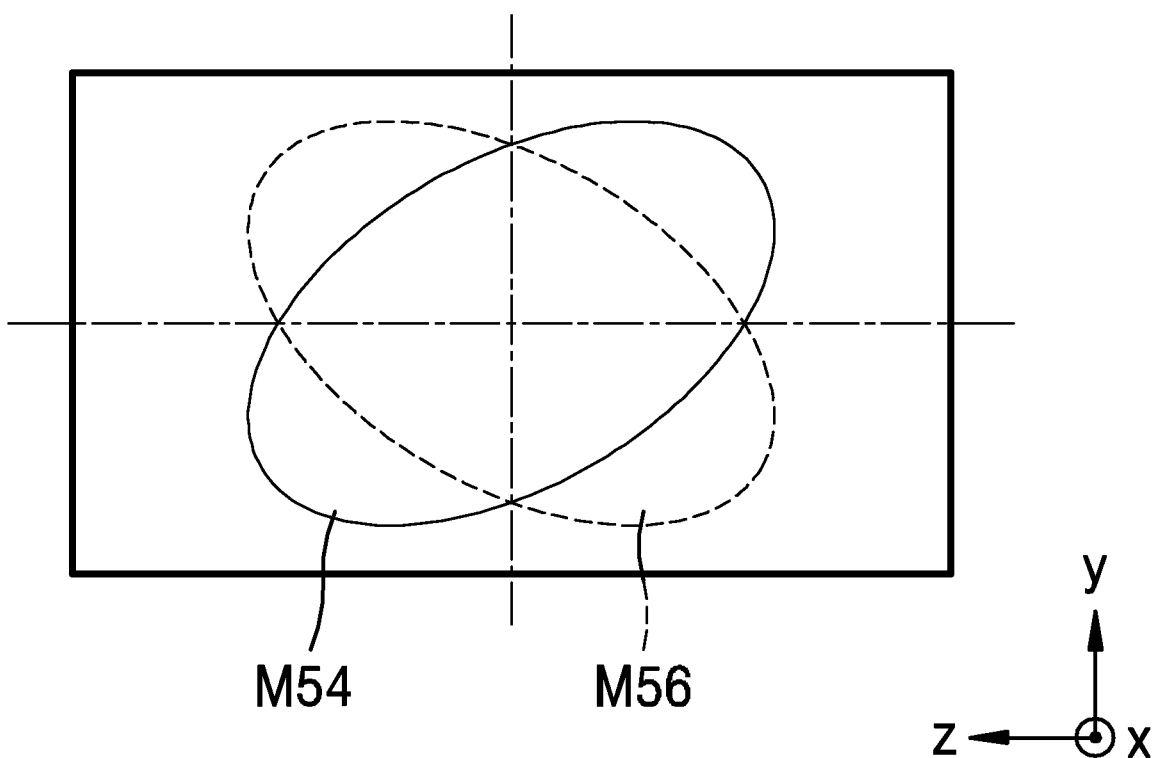
FIG. 5B illustrates magnetic fields formed by the RF coil of FIG. 5A according to another embodiment of the present invention.

FIG. 5A illustrates an RF coil 50 according to another embodiment of the present invention. FIG. 5B illustrates magnetic fields M54 and M56 formed by the RF coil 50 of FIG. 5A according to another embodiment of the present invention.

Referring to FIG. 5A, the RF coil 50 according to an embodiment may include a first RF coil element 54 and a second RF coil element 56 that are formed on a base 52. The first RF coil element 54 and the second RF coil element 56 may differently protrude in a z axis direction. Specifically, the first RF coil element 54 may include an RF coil element protruding in a top right direction and a bottom left direction on a z-y plane with respect to a lateral or sagittal view, and the second RF coil element 56 may include an RF coil element protruding in a top left direction and a bottom right direction on the z-y plane with respect to the lateral or sagittal view. Accordingly, shapes of magnetic fields formed by the first RF coil element 54 and the second RF coil element 56 may alternate each other on the z-y plane. FIG. 5B illustrates the magnetic fields M54 and M56 formed by the RF coil of FIG. 5A.

Referring to FIGS. 5A and 5B, the magnetic fields M54 and M56 respectively formed by the first RF coil element 54 and the second RF coil element 56 may alternate each other in a diagonal direction. As described above, shapes of RF coil elements of an RF coil may be arbitrarily adjusted and may be selectively applied according to an ROI of an object that is an examination target. An insulating layer for maintaining an electrical insulation may be formed between the first RF coil element 54 and the second RF coil element 56.

As described above, an MRI system according to an embodiment may variously modify an RF coil according to a location of an ROI of an object that is an examination target, and may enhance homogeneity of a magnetic field formed irrespective of the location of the ROI of the object.

It should be understood that the embodiments described herein should be considered in a descriptive sense only and not for purposes of limitation. Descriptions of features or aspects within each embodiment should typically be considered as available for other similar features or aspects in other embodiments. For example, the RF coil according to the present disclosure may be applied to a volume-type RF coil of an MRI system and may also be applied to a body-type RF coil.

While one or more embodiments have been described with reference to the figures, it will be understood by those of ordinary skill in the art that various changes in form and details may be made therein without departing from the spirit and scope as defined by the following claims.

The invention claimed is:

1. A bird-cage radio frequency (RF) coil for a magnetic resonance imaging (MRI) system, the bird-cage RF coil comprising:
a RF coil element of a first end portion and a RF coil element of a second end portion are formed on an outer circumferential portion of a cylinder having a circular or oval cross-sectional shape; and
connectors formed by connecting the RF coil element of the first end portion and the RF coil element of the second end portion,
wherein the RF coil element of the first end portion and the RF coil element of the second end portion are bent perpendicularly in a z axis direction and the bent portions extending away from an axial center of the bird-cage RF coil, wherein the z axis direction is aligned in a longitudinal direction of the bird-cage RF coil,
wherein the RF coil element of the first end portion and the RF coil element of the second end portion surround alternating regions of the first end portion and the second end portion of the cylinder, respectively, and
wherein a second distance between the RF coil element of the second end portion from an axial center of the bird-cage RF coil is less than a first distance between the RF coil element of the first end portion from the axial center of the bird-cage RF coil.

2. The bird-cage RF coil of claim 1, wherein the bird-cage RF coil forms a magnetic field of an asymmetrical shape in the z direction with respect to a y axis on a z-y plane.

3. The bird-cage RF coil of claim 1, wherein the connectors are formed in a straight line shape in the z axis direction between the RF coil element of the first end portion and the RF coil element of the second end portion.

4. The bird-cage RF coil of claim 1, wherein between 8 and 32 connectors are formed.

5. The bird-cage RF coil of claim 1, wherein shapes of magnetic fields, formed by the RF coil element of the first end portion and the RF coil element of the second end portion, alternate with each other in respective diagonal directions on a z-y plane.

6. The bird-cage RF coil of claim 1, wherein an insulating layer is formed between the RF coil element of the first end portion and the RF coil element of the second end portion in order to maintain an electrical insulation.

7. The bird-cage RF coil of claim 1, wherein the bird-cage RF coil is a volume-type RF coil.

8. An MRI system comprising:
an bird-cage radio frequency (RF) coil comprising:
a RF coil element of a first end portion and a RF coil element of a second end portion are formed on an outer circumferential portion of a cylinder having a circular or oval cross-sectional shape; and
connectors formed by connecting the RF coil element of the first end portion and the RF coil element of the second end portion,
wherein the RF coil element of the first end portion and the RF coil element of the second end portion are bent perpendicularly in a z axis direction and the bent portions extending away from an axial center of the bird-cage RF coil, wherein the z axis direction is aligned in a longitudinal direction of the bird-cage RF coil,
wherein the RF coil element of the first end portion and the RF coil element of the second end portion surround alternating regions of the first end portion and the second end portion of the cylinder, respectively, and
wherein a second distance between the RF coil element of the second end portion from an axial center of the bird-cage RF coil is less than a first distance between the RF coil element of the first end portion from the axial center of the bird-cage RF coil.

9. The MRI system of claim 8, wherein the bird-cage RF coil forms a magnetic field of an asymmetrical shape in a z direction with respect to a y axis on a z-y plane.

10. The MRI system of claim 8, wherein shapes of magnetic fields, formed by the RF coil element of the first end portion and the RF coil element of the second end portion, alternate with each other in respective diagonal directions on a z-y plane.

11. The MRI system of claim 8, wherein the bird-cage RF coil is a volume-type RF coil located on a table on which an object is located.

12. An MRI system comprising:
    a gradient coil; and
    a bird-cage radio frequency (RF) coil formed on a cylindrical base having a circular or oval cross-sectional shape,
        wherein the bird-cage RF coil comprises first and second end portions each respectively traversing a circumferential region of axially opposite portions of the cylindrical base, wherein the first end portion and second end portion vary in distance from an axial center of the bird-cage RF coil, and
        wherein an RF coil element of the first end portion and an RF coil element of the second end portion are bent perpendicularly in a z axis direction and the bent portions extending away from the axial center, and
        wherein a second distance between the RF coil element of the second end portion from an axial center of the bird-cage RF coil is less than a first distance between the RF coil element of the first end portion from the axial center of the bird-cage RF coil.

13. The MRI system of claim 12, wherein the first and second end portions include serially connected capacitors.

14. The MRI system of claim 12, wherein the bird-cage RF coil forms a magnetic field of an asymmetrical shape in the z direction with respect to a y axis on a z-y plane, wherein the z direction is a direction parallel with an axis of the base.

15. The MRI system of claim 12, wherein the bird-cage RF coil comprises connectors formed to each connect the first and second end portions at different circumferential positions of the bird-cage RF coil.

16. The MRI system of claim 12, wherein the bird-cage RF coil has a twisted shape with the first end portion and the second end portion each having right angle sections.

17. The MRI system of claim 12, shapes of magnetic fields formed by the RF coil element of the first end portion and the RF coil element of the second end portion respectively alternate with each other in respective diagonal directions on a z-y plane, where the z axis is parallel with an electric field generated by the bird-cage RF coil.

18. The MRI system of claim 12, wherein the bird-cage RF coil is a volume-type bird-cage RF coil.

19. A bird-cage radio frequency (RF) coil for a magnetic resonance imaging (MRI) system, the bird-cage RF coil comprising:
    a RF coil element of a first end portion and a RF coil element of a second end portion are formed on an outer circumferential portion of a cylinder having a circular or oval cross-sectional shape; and
    connectors formed by connecting the RF coil element of the first end portion and the RF coil element of the second end portion,
        wherein the RF coil element of the first end portion and the RF coil element of the second end portion are bent perpendicularly in a z axis direction and the bent portions extending away from an axial center of the bird-cage RF coil, wherein the z axis direction is aligned in a longitudinal direction of the bird-cage RF coil,
        wherein the bird-cage RF coil forms a magnetic field of an asymmetrical shape in the z direction with respect to a y axis on a z-y plane,
        wherein the RF coil element of the first end portion and the RF coil element of the second end portion surround alternating regions of the first end portion and the second end portion of the cylinder, respectively, and
        wherein a second distance between the RF coil element of the second end portion from an axial center of the bird-cage RF coil is less than a first distance between the RF coil element of the first end portion from the axial center of the bird-cage RF coil.

\* \* \* \* \*